United States Patent [19]

Evenson

[11] 4,086,230
[45] Apr. 25, 1978

[54] 1,5-DIHYDRO-7-ARYL-AS-TRIAZINE[4,3,-a][1,4]BENZODIAZEPIN-1-OLS

[75] Inventor: Gerald N. Evenson, Cooper Township, Kalamazoo County, Mich.

[73] Assignee: The Upjohn Company, Kalamazoo, Mich.

[21] Appl. No.: 775,887

[22] Filed: Mar. 9, 1977

[51] Int. Cl.² ............... A61K 31/55; C07D 405/06; C07D 487/04
[52] U.S. Cl. .................. 260/243.3; 260/239 BD; 260/296 B; 260/340.7; 260/340.9 R; 424/244; 424/249; 424/278
[58] Field of Search .............. 260/248 AS, 243.3

[56] References Cited

U.S. PATENT DOCUMENTS

| | | | |
|---|---|---|---|
| 3,818,003 | 6/1974 | Szmuszkovicz | 260/248 AS |
| 3,882,112 | 5/1975 | Szmuszkovicz | 260/248 AS |
| 3,933,816 | 1/1976 | Szmuszkovicz | 260/248 AS |
| 4,016,165 | 4/1977 | Moffett | 260/248 AS |
| 4,017,492 | 4/1977 | Moffett | 260/248 AS |
| 4,028,356 | 6/1977 | Moffett | 260/248 AS |

OTHER PUBLICATIONS

Moffett III, Letters on Heterocyclic Chemistry, vol. 3, pp. 3449–3456 (1976).

*Primary Examiner*—Alton D. Rollins
*Attorney, Agent, or Firm*—Hans L. Berneis

[57] ABSTRACT

Compounds of the formula:

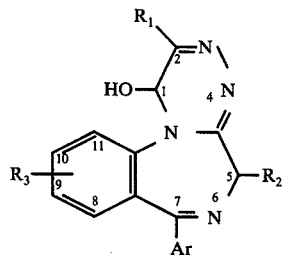

wherein $R_1$ is alkyl of 1 to 3 carbon atoms, inclusive; wherein $R_2$ is hydrogen, methyl or ethyl; wherein $R_3$ is hydrogen, fluoro, chloro, bromo, nitro and $-CF_3$; and wherein Ar is phenyl, o-chlorophenyl, o-fluorophenyl, 2,6-difluorophenyl, and 2-pyridyl, are prepared by treating a hydrazino compound of the formula:

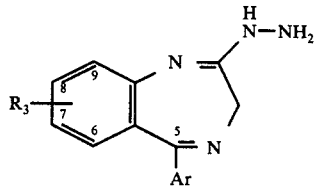

with a carbonyl compound II:

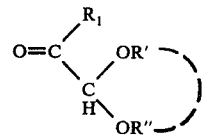

wherein $R_1$ is defined as above, and R', R" are alkyl of 1 to 3 carbon atoms, inclusive, or the group

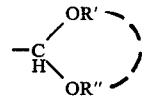

is a cyclic acetal, such as

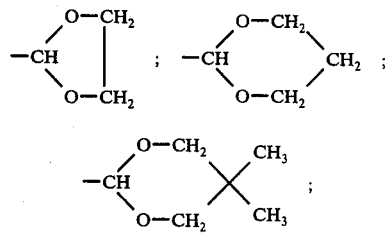

to give a compound of formula III:

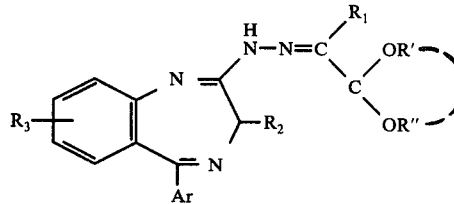

wherein $R_1$, $R_2$, $R_3$, R', R" and Ar are defined as above, and cyclizing compound III to give the compound IV above.

Compounds III and IV, including the pharmacologically acceptable acid addition salt of these compounds, have sedative, anxiolytic and muscle-relaxing activity and can be used for the treatment of anxieties or muscle strains of mammals, including man.

10 Claims, No Drawings

1,5-DIHYDRO-7-ARYL-AS-TRIAZINE[4,3,-a][1,4]BENZODIAZEPIN-1-OLS

BACKGROUND OF THE INVENTION

Field of the Invention

This invention is directed to new organic compounds and is particularly concerned with 1-hydroxyas-triazinobenzodiazepines of formula IV, intermediates thereto of formula III, and the process therefor.

The novel compounds and process of production therefor can be illustratively represented as follows:

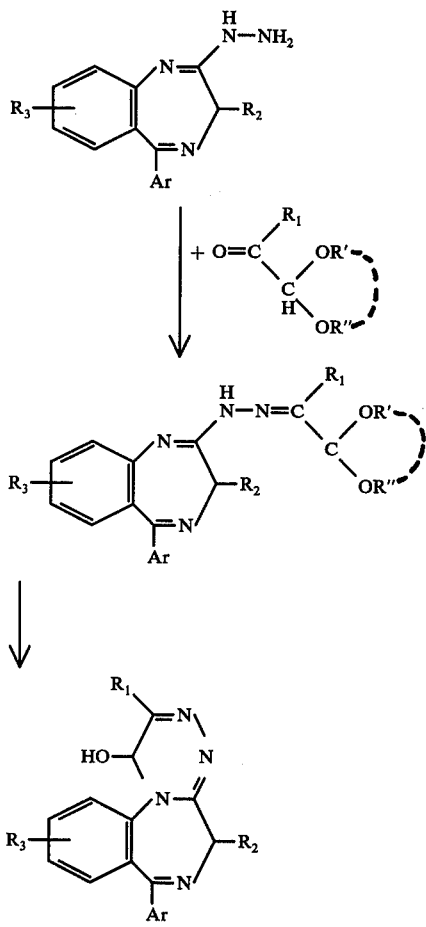

wherein R′, R″ are alkyl of 1 to 3 carbon atoms, inclusive, or the group

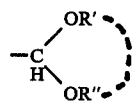

together is

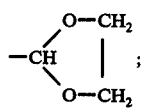

-continued

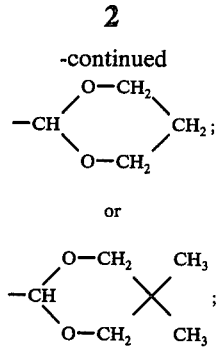

wherein $R_1$ is alkyl of 1 to 3 carbon atoms, inclusive; wherein $R_2$ is hydrogen, methyl or ethyl; wherein $R_3$ is hydrogen, fluoro, chloro, bromo, nitro and $-CF_3$; and wherein Ar is phenyl, o-chlorophenyl, o-fluorophenyl, 2,6-difluorophenyl, and 2-pyridyl.

The process of this invention comprises: treating a hydrazino compound of formula I with a carbonyl reagent of formula II to obtain the corresponding compound of formula III; and treating compound III with a cyclizing reagent to obtain the corresponding compound of formula IV.

The invention claims the compounds of formulae III and IV, the process to make these compounds and the pharmacologically acceptable acid addition salts thereof.

DESCRIPTION OF THE PREFERRED EMBODIMENT

Alkyl groups of 1 to 3 carbon atoms, inclusive, are exemplified by methyl, ethyl, propyl and isopropyl.

The more preferred compounds of this invention are of the formula IIIA and IVA:

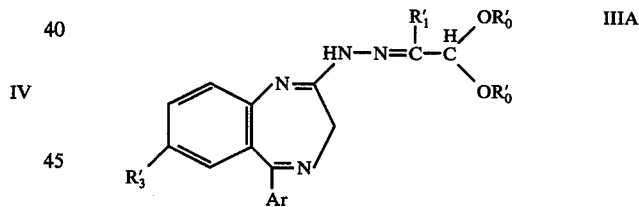

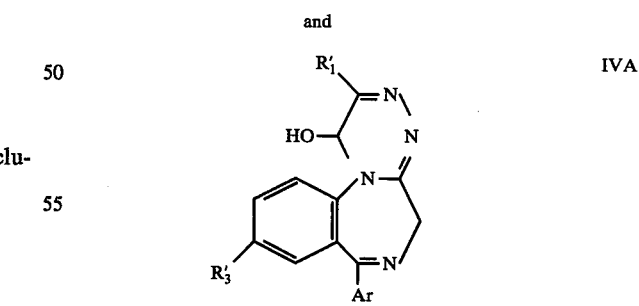

wherein $R_1'$ is methyl or ethyl; wherein $R_3'$ is fluoro, chloro, bromo, or trifluoromethyl; wherein $R_o'$ is alkyl of 1 to 3 carbon atoms, inclusive; and wherein Ar is phenyl, o-chlorophenyl, o-fluorophenyl, 2,6-difluorophenyl or 2-pyridyl, and the pharmacologically acceptable acid addition salts thereof.

The most preferred compounds of this invention are of the formula IIIB and IVB:

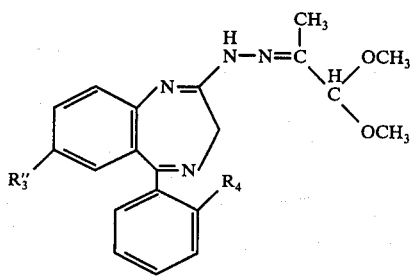

IIIB and

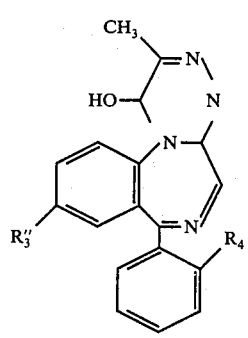

IVB wherein $R_3''$ is fluoro, chloro or trifluoromethyl, and wherein $R_4$ is hydrogen, chloro or fluoro, and the pharmacologically acceptable acid addition salts thereof.

Compounds of formula III and IV (including IIIA, IIIB, and IVA and IVB) are sedative, tranquilizing, anxiolytic, muscle-relaxing and anti-convulsive agents which are useful for treating anxieties, convulsions or strained muscles in mammals, including man.

The sedative-tranquilizing-anxiolytic activity was evaluated in compounds of formula III and IV by the following test:

Gamma Butyrolactone Sleep Potentiation

Gamma butyrolactone produces loss of righting in mice at doses higher than 400 mg./kg. intraperitoneally. At lower doses (200 mg./kg.) the mice do not lose their righting reflex unless previously treated with sub-hypnotic doses of central nervous system depressant agents. This then provides a technique to study the depressant activity of potential central nervous system agents.

Method

The test compound is injected intraperitoneally 50 mg./kg. into a group of four mice and thirty minutes later gamma-butyrolactone is injected intraperitoneally, 200 mg./kg. (normally a sub-hypnotic dose). After ten minutes, the mice are tested for loss of righting reflex. If more than two mice show a loss of righting for one minute or more, the compound is retested at multiple dose levels.

Anti-convulsion Test

Protection Against Bicucullin-Induced Tonic Extensor Convulsions

In this procedure, groups of four Carworth Farms male mice, weighing 18–22 g. each, are injected intraperitoneally with the test agent prepared in 0.25% methylcellulose. Thirty minutes later, bicucullin is injected intravenously at 1 mg./kg. Bicucullin is solubilized in 1N hydrochloric acid and diluted to a concentration of 1–4 mg./ml. with physiological saline and adjusted to a final pH of 5–6 before injection. Mice are observed for 5 minutes after bicucullin injection. A compound is considered to be active if it protects at least 2 of the 4 mice from tonic extensor convulsions during this period. Active compounds are retested using multiple dose levels decreasing at 0.3 or 0.5 log intervals and the number of mice failing to convulse is used as a quantal response to calculate the $ED_{50}$ (Spearman and Karber: Finney, D. J., Statistical Method in Biological Assay, Hafner Publ. Co., N.Y., p. 524, 1952). This procedure is a useful test for detecting compounds with minor tranquilizer or sedative activity.

Anti-convulsant, Muscular Relaxing Activity by the Pentylenetetrazol (Metrazol) Test Metrazol Induced Convulsion Test The test compound is injected intraperitoneally (50 mg./kg.) into groups of four mice at multiple dose levels decreasing in 0.3 log intervals. Thirty minutes later Metrazol is injected subcutaneously (at the nape of the neck), 85 mg./kg. Fifteen minutes later a set of keys is rattled over the cage to induce the clonic convulsions. The number of mice protected against convulsions and death is recorded.

Thus, these compounds are useful for tranquilization, sedation, treating anxieties, and also useful as anti-convulsant and muscle relaxants in mammals and birds.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers, such as carbohydrates (lactose), proteins, lipids, calcium phosphate, corn starch, stearic acid, methylcellulose and the like may be used as carriers or form coating purposes. Water or oil, e.g., coconut oil, sesame oil, safflower oil, cottonseed oil, peanut oil, may be used for preparing solutions or suspensions of the active drug. Sweetening, coloring and flavoring agents may be added.

For mammals and birds, food premixes with starch, oatmeal, dried fishmeat, fishmeal, flour and the like can be prepared.

The compounds of formulae III and IV can be used in dosages of 0.05–1 mg./kg./day; preferably in unit dosages of 0.1–1 mg./kg./day in oral or injectable preparations as described above, to alleviate tension and anxiety, muscle spasm or convulsions in mammals, or birds, such as e.g., occurs when animals are in travel.

The starting materials of formula I of this invention, a 5-phenyl- or substituted phenyl group, are known in the art, e.g., from Canadian Pat. No. 908,657.

The compounds of formula I which have a 2-pyridyl group in the 5-position can be made from the corresponding 2-thiones according to U.S. Pat. No. 3,996,230.

In carrying out the process of this invention, a compound of formula I is reacted with a carbonyl compound of formula II. The reaction is generally carried out in an organic solvent, inert in this reaction, e.g., dioxane, tetrahydrofuran, diethyl ether, ethanol, benzene, toluene, or the like. The type of carbonyl compound selected depends on the alkyl group desired in position 2 of final compounds of formula IV. 1,1-Dialkoxy-2-propanone provides a 2-methyl group in compounds of formula IV, the 2-butanones provide an ethyl group and the 2-pentanones are productive of a propyl group in the 2-position. The alkoxy groups in these 1,1-dialkoxy-2-alkanones can be methoxy, ethoxy, or propoxy, with methoxy preferred. In the preferred embodiment of this invention, the alkanone II is used in a stoichiometric excess like 1,5 to 5 times the calculated equimolar amount to one mole equivalent of the hydrazino compound I. The temperature of the reaction is between 10°–50° C., preferably room temperature, and the reaction period is between 2–48 hours, with 12 to 24 hours usually sufficient at room temperature (20° to 25° C.). After termination of the reaction, the product (III) is isolated and purified in conventional manner, such as by precipitation and filtration, extraction, chromatography and recrystallization.

Compound III is cyclized to give compound IV with concentrated sulfuric acid (neat), sulfuric acid in Sulfolane, or anhydrous hydrogen fluoride, with concentrated sulfuric acid preferred. Low temperatures (−20° to +10° C. at the start with 10° to 40° C. in the later stage) are preferred for this reaction. The reaction period is between ½ to 6 hours, with 1 to 4 hours being usually sufficient. Thereafter the reaction mixture is neutralized and the product IV is obtained by extraction. Compound IV is purified in conventional manner, e.g., chromatography and recrystallizations.

The following Preparation and Examples are illustrative of the process and the compounds of the present invention, but are not to be construed to be limiting.

In the manner given in U.S. Pat. No. 3,996,230 1,3-dihydro-2-hydrazino-5-(2-pyridyl)-2H-1,4-benzodiazepines can be prepared. Representative compounds, thus prepared, include: 7-chloro-1,3-dihydro-2-hydrazino-5-(2-pyridyl)-2H-1,4-benzodiazepine, 7-fluoro-1,3-dihydro-2-hydrazino-5-(2-pyridyl)-2H-1,4-benzodiazepine, 7-nitro-1,3-dihydro-2-hydrazino-5-(2-pyridyl)2H-1,4-benzodiazepine, 8-bromo-1,3-dihydro-2-hydrazino-5-(2-pyridyl)-2H-1,4-benzodiazepine, 8-fluoro-1,3-dihydro-2-hydrazino-5-(2-pyridyl)-2H-1,4-benzodiazepine, 8-chloro-1,3-dihydro-2-hydrazino-5-(2-pyridyl)-2H-1,4-benzodiazepine, 9-trifluoromethyl-1,3-dihydro-2-hydrazino-5-(2-pyridyl)-2H-1,4-benzodiazepine, 9-bromo-1,3-dihydro-2-hydrazino-5-(2-pyridyl)-2H-1,4-benzodiazepine, 8-nitro-1,3-dihydro-2-hydrazino-5-(2-pyridyl)-2H-1,4-benzodiazepine, 9-nitro-1,3-dihydro-2-hydrazino-5-(2-pyridyl)-2H-1,4-benzodiazepine, 7-trifluoromethyl-1,3-dihydro-2-hydrazino-5-(2-pyridyl)-2H-1,4-benzodiazepine, and the like.

EXAMPLE 1

1,1-Dimethoxy-2-propanone, 2-(7-chloro-5-phenyl-3H-1,4-benzodiazepin-2-yl)hydrazone A solution of 2.84 g. (0.01 mole) of 7-chloro-2-hydrazino-5-phenyl-3H-1,4-benzodiazepine and 2.6 g. (0.022 mole) of 1,1-dimethoxy-2-propanone in 100 ml. of tetrahydrofuran was stirred at room temperature for 18 hours and evaporated in vacuo. The residue was dissolved in methylene chloride, washed with water and dried over anhydrous sodium sulfate. After filtration and concentration the product was chromatographed on silica gel, eluting with a mixture of hexane 22%, methylene chloride 76% and 2-propanol 2%. The product was crystallized from a mixture of ethyl acetate and hexane yielding 2.3 g. (60%) of 1,1-dimethoxy-2-propane, 2-(7-chloro-5-phenyl-3H-1,4-benzodiazepin-2-yl)hydrazone of melting point 182°–183° C.

Anal. Calcd. for $C_{20}H_{21}ClN_4O_2$: C, 62.41; H, 5.50; Cl, 9.21; N, 14.56 Found: C, 62.62; H, 5.55; Cl, 9.16; N, 14.72

EXAMPLE 2

9-Chloro-1,5-dihydro-2-methyl-7-phenyl-astriazino[4,3-a][1,4]benzodiazepin-1-ol

To 15 ml. of concentrated sulfuric acid, at 0° C. under nitrogen, was slowly added with stirring 2.52 g. (0.065 mole) of 1,1-dimethoxy-2-propanone, 2-(7-chloro-5-phenyl-3H-1,4-benzodiazepine-2-yl)hydrazone. The solution was allowed to warm to room temperature, stirred for 2 hours, quenched with ice and aqueous sodium bicarbonate solution, and extracted with methylene chloride. After washing with water, drying over anhydrous sodium sulfate and evaporating in vacuo the residue was crystallized from a mixture of methylene chloride, methanol and ethyl acetate. More product was obtained by chromatographing the filtrate on silica gel, eluting with 10% (volume) methanol in chloroform and crystallizing from ethyl acetate. The total yield was 1.15 g. (about 50%) of 9-chloro-1,5-dihydro-2-methyl-7-phenyl-as-triazino[4,3-a][1,4]benzodiazepin-1-ol of melting point 170° – 172° C. (dec.), containing ethyl acetate. The compound seems to solvate with many solvents and the decomposition points varied widely. A sample for analysis was crystallized from ethyl acetate-methanol and was found to contain about 0.8 mole of methanol even after long drying in vacuo, melting point 170°– 174° C. (dec.).

Anal. Calcd. for $C_{18}H_{15}ClN_4O \cdot 0.8\ CH_3OH$: C, 61.96; H, 5.03; Cl, 9.73; N, 15.37; MeOH, 7.03 Found: C, 61.54; H, 5.02; Cl, 9.73; N, 15.69; melt solvate), 6.81 (MeOH).

EXAMPLE 3

1,1-Dimethoxy-2-propanone,2-[7-chloro-5-(o-chlorophenyl)-3H-1,4-benzodiazepin-2-yl]hydrazone Following Example 1, 15.96 g. (0.05 mole) of 7-chloro-5-(o-chlorophenyl)-2-hydrazino-3H-1,4-benzodiazepine and 11.8 g. (0.1 mole) of 1,1-dimethoxy-2-propanone in 250 ml. of tetrahydrofuran were reached together. The product was crystallized from ethyl acetate-hexane and additional material was obtained by chromatographing the filtrate on silica gel, eluting with 5% methanol in chloroform. The total yield was 17.0 g. (81%) of 1,1-dimethoxy-2-propanone,2-[7-chloro-5-(o-chlorophenyl)-3H-1,4-benzodiazepin-2-yl]hydrazone of melting point 153° – 158° C. The sample for analysis, recrystallized from ethyl acetate-hexane, had a melting point of 157° – 158° C.

Anal. Calcd. for $C_{20}H_{20}Cl_2N_4O_2$: C, 57.28; H, 4.81; Cl, 16.91; N, 13.36 Found: C, 57.55; H, 4.95; Cl, 16.95; N, 13.20

EXAMPLE 4

9-Chloro-7-(o-chlorophenyl)-1,5-dihydro-2-methyl-as-triazino[4,3-a][1,4]benzodiazepin-1-ol Following Example 2, 7.57 g. (0.018 mole) of 1,1-dimethoxy-2-propanone,2-[7-chloro-5-(o-chlorophenyl)-3H-1,4-benzodiazepin-2-yl]hydrazone and 30 ml. of concentrated sulfuric acid were reacted. The product was crystallized from ethyl acetate yielding 4.08 (60%) of crystalline solid, 9-chloro-7-(o-chlorophenyl)-1,5-dihydro-2-methyl-as-triazino[4,3-a][1,4]benzodiazepin-1-ol of melting point 170° – 173° C. (dec.). A nuclear magnetic resonance spectrum showed the presence of ethyl acetate of crystallization. A sample for analysis was crystallized from a mixture of ethyl acetate and methylene chloride, melting point 165° – 170° C. (dec.).

Anal. Calcd. for $C_{18}H_{14}Cl_2N_4O\cdot0.08$ EtOAc·0.04 $CH_2Cl_2$: C, 57.62; H, 3.87; Cl, 19.01; N, 14.64; EtOAc, 1.84; $CH_2Cl_2$, 0.89. Found: C, 57.00; H, 3.72; Cl, 18.58; N, 14.71; melt solvate EtOAc, 1.68; $CH_2Cl_2$, 0.82.

EXAMPLE 5

1,1-Diethoxy-2-butanone, 2-[7-fluoro-5-(o-chlorophenyl)-3H-1,4-benzodiazepin-2-yl]hydrazone In the manner given in Example 1, 7-fluoro-2-hydrazino-5-(o-chlorophenyl)-3H-1,4-benzodiazepine can be reacted with 1,1-diethoxy-2-butanone in tetrahydrofuran to give 1,1-diethoxy-2-butanone, 2-[7-fluoro-5-(o-chlorophenyl)-3H-1,4-benzodiazepin-2 -yl]hydrazone.

EXAMPLE 6

9-Fluoro-1,5-dihydro-2-ethyl-7-(o-chlorophenyl)-as-triazino[4,3-a][1,4]benzodiazepin-1-ol In the manner given in Example 2, 1,1-diethoxy-2-butanone 2-[7-fluoro-5-(o-chlorophenyl)-3H-1,4-benzodiazepin-2-yl]hydrazone can be treated at 0° C. under nitrogen with concentrated sulfuric acid to give 9-fluoro-1,5-dihydro-2-ethyl-7-(o-chlorophenyl)-as-triazino[4,3-a]-[1,4]benzodiazepin-1-ol.

EXAMPLE 7

1,1-Dimethoxy-2-propanone, 2-[7-bromo-5-(2-pyridyl)-3H-1,4-benzodiazepin-2-yl]hydrazone In the manner given in Example 1, 7-bromo-2-hydrazino-5-(2-pyridyl)-3H-1,4-benzodiazepine can be reacted with 1,1-dimethoxy-2-propanone in tetrahydrofuran to give 1,1-dimethoxy-2-propanone, 2-[7-bromo-5-(2-pyridyl)-3H-1,4-benzodiazepin-2-yl]hydrazone.

EXAMPLE 8

9-Bromo-1,5-dihydro-2-methyl-7-(2-pyridyl)-as-triazino[4,3-a][1,4]benzodiazepin-1-ol In the manner given in Example 2, 1,1-dimethoxy-2-propanone, 2-[7-bromo-5-(2-pyridyl)-3H-1,4-benzodiazepin-2-yl]hydrazone can be treated at 0° C. under nitrogen with concentrated sulfuric acid to give 9-bromo-1,5-dihydro-2-methyl-7-(2-pyridyl)-as-triazino[4,3-a][1,4]benzodiazepin-1-ol.

EXAMPLE 9

1,1-Dipropoxy-2-pentanone, 2-(7-trifluoromethyl-5-phenyl-3H-1,4-benzodiazepin-2-yl)hydrazone In the manner given in Example 1, 7-trifluoromethyl-2-hydrazino-5-phenyl-3H-1,4-benzodiazepine can be reacted with 1,1-dipropoxy-2-pentanone in tetrahydrofuran to give 1,1-dipropoxy-2-pentanone, 2-(7-trifluoromethyl-5-phenyl-3H-1,4-benzodiazepin-2-yl)hydrazone.

EXAMPLE 10

9-Trifluoromethyl-1,5-dihydro-2-propyl-7-phenyl-as-triazino[4,3-a][1,4]benzodiazepin-1-ol In the manner given in Example 2, 1,1-dipropoxy-2-pentanone, 2-(7-trifluoromethyl-5-phenyl-3H-1,4-benzodiazepin-2-yl)hydrazone can be treated at 0° C. under nitrogen with concentrated sulfuric acid to give 9-trifluoromethyl-1,5-dihydro-2-propyl-7-phenyl-as-triazino[4,3-a][1,4]benzodiazepin-1-ol.

EXAMPLE 11

1,1-Dimethoxy-2-propanone, 2-[5-(o-chlorophenyl)-3H-1,4-benzodiazepin-2-yl]hydrazone In the manner given in Example 1, 2-hydrazino-5-(o-chlorophenyl)-3H-1,4-benzodiazepine can be reacted with 1,1-dimethoxy-2-propanone in tetrahydrofuran to give 1,1-dimethoxy-2-propanone, 2-[5-(o-chlorophenyl)-3H-1,4-benzodiazepin-2-yl]hydrazone.

EXAMPLE 12

7-(o-Chlorophenyl)-1,5-dihydro-2-methyl-as-triazino[4,3-a][1,4]benzodiazepin-1-ol In the manner given in Example 2, 1,1-dimethoxy-2-propanone, 2-[5-(o-chlorophenyl)-3H-1,4-benzodiazepin-2-yl]hydrazone can be treated at 0° C. under nitrogen with concentrated sulfuric acid to give 7-(o-chlorophenyl)-1,5-dihydro-2-methyl-as-triazino[4,3-a][1,4]benzodiazepin-1-ol.

EXAMPLE 13

1,1-Diethoxy-2-propanone, 2-[7-nitro-5-(o-chlorophenyl)-3H-1,4-benzodiazepin-2-yl]hydrazone In the manner given in Example 1, 7-nitro-2-hydrazino-5-(o-chlorophenyl)-3H-1,4-benzodiazepine can be reacted with 1,1-diethoxy-2-propanone in tetrahydrofuran to give 1,1-diethoxy-2-propanone, 2-[7-nitro-5-(o-chlorophenyl)-3H-1,4-benzodiazepin-2-yl]hydrazone.

EXAMPLE 14

9-Nitro-1,5-dihydro-2-methyl-7-(o-chlorophenyl)-as-triazino[4,3-a][1,4]benzodiazepin-1-ol In the manner given in Example 2, 1,1-diethoxy-2-propanone, 2-[7-nitro-5-(o-chlorophenyl)-3H-1,4-benzodiazepin-2-yl]hydrazone can be treated at 0° C. under nitrogen with concentrated sulfuric acid to give 9-nitro-1,5-dihydro-2-methyl-7-(o-chlorophenyl)-as-triazino[4,3-a][1,4]benzodiazepin-1-ol.

EXAMPLE 15

1,1-Dimethoxy-2-butanone, 2-[7-chloro-5-(2,6-difluorophenyl)-3H-1,4-benzodiazepin-2-yl]hydrazone In the manner given in Example 1, 7-chloro-2-hydrazino-5-(2,6-difluorophenyl)-3H-1,4-benzodiazepine can be reacted with 1,1-dimethoxy-2-butanone in tetrahydrofuran to give 1,1-dimethoxy-2-butanone, 2-[7-chloro-5-(2,6-difluorophenyl)-3H-1,4-benzodiazepin-2-yl]hydrazone.

EXAMPLE 16

9-Chloro-1,5-dihydro-2-ethyl-7-(2,6-difluorophenyl)-as-triazino[4,3a][1,4]benzodiazepin-1-ol In the manner given in Example 2, 1,1-dimethoxy-2-butanone, 2-[7-chloro-5-(2,6-difluorophenyl)-3H-1,4-benzodiazepin-2-yl]hydrazone can be treated at 0° C. under nitrogen with concentrated sulfuric acid to give 9-chloro-1,5-dihydro-2-ethyl-7-(2,6-difluorophenyl)-as-triazino[4,3-a][1,4]benzodiazepin-1-ol.

EXAMPLE 17

1,1-Dimethoxy-2-pentanone, 2-[6-bromo-5-(o-fluorophenyl)-3H-1,4-benzodiazepin-2-yl]hydrazone In the manner given in Example 1, 6-bromo-2-hydrazino-5-(o-fluorophenyl)-3H-1,4-benzodiazepine can be reacted with 1,1-dimethoxy-2-pentanone in tetrahydrofuran to give 1,1-dimethoxy-2-pentanone, 2-[6-bromo-5-(o-fluorophenyl)-3H-1,4-benzodiazepin-2-yl]hydrazone.

EXAMPLE 18

8-Bromo-1,5-dihydro-2-propyl-7-(o-fluorophenyl)-as-triazino[4,3-a][1,4]benzodiazepin-1-ol In the manner given in Example 2, 1,1-dimethoxy-2-pentanone, 2-[6-bromo-5-(o-fluorophenyl)-3H-1,4-benzodiazepin-2-yl]hydrazone can be treated at 0° C. under nitrogen with concentrated sulfuric acid to give 8-bromo-1,5-dihydro-2-propyl-7-(o-fluorophenyl)-as-triazino[4,3-a][1,4]benzodiazepin-1-ol.

EXAMPLE 19

1,1-Dimethoxy-1-butanone, 2-[8-fluoro-5-phenyl-3H-1,4-benzodiazepin-2-yl]hydrazone In the manner given in Example 1, 8-fluoro-2-hydrazino-5-phenyl-3H-1,4-benzodiazepine can be reacted with 1,1-dimethoxy-2-butanone in tetrahydrofuran to give 1,1-dimethoxy-2-butanone, 2-(8-fluoro-5-phenyl-3H-1,4-benzodiazepin-2-yl)hydrazone.

EXAMPLE 20

10-Fluoro-1,5-dihydro-2-ethyl-7-phenyl-as-triazino[4,3-a][1,4]benzodiazepin-1-ol In the manner given in Example 2, 1,1-dimethoxy-2-butanone, 2-(8-fluoro-5-phenyl-3H-1,4-benzodiazepin-2yl)hydrazone can be treated at 0° C. under nitrogen with concentrated sulfuric acid to give 10-fluoro-1,5-dihydro-2-ethyl-7-phenyl-as-triazino[4,3-a][1,4]benzodiazepin-1-ol.

EXAMPLE 21

1,1-Diethoxy-2-propanone, 2-[8-chloro-5-(o-chlorophenyl]-3H-1,4-benzodiazepin-2-yl]hydrazone In the manner given in Example 1, 8-chloro-2-hydrazino-5-(o-chlorophenyl)-3H-1,4-benzodiazepine can be reacted with 1,1-diethoxy-2-propanone in tetrahydrofuran to give 1,1-diethoxy-2-propanone, 2-[8-chloro-5-(o-chlorophenyl)-3H-1,4-benzodiazepin-2-yl]hydrazone.

EXAMPLE 22

10-Chloro-1,5-dihydro-2-methyl-7-(o-chlorophenyl)-as-triazino[4,3-a][1,4]benzodiazepin-1-ol In the manner given in Example 2, 1,1-diethoxy-2-propane, 2-[8-chloro-5-(o-chlorophenyl)-3H-1,4-benzodiazepin-2-yl]hydrazone can be treated at 0° C. under nitrogen with concentrated sulfuric acid to give 10-chloro-1,5-dihydro-2-methyl-7-(o-chlorophenyl)-as-triazino[4,3-a][1,4]benzodiazepin-1-ol.

EXAMPLE 23

1,1-Dimethoxy-2-propanone, 2-[7-chloro-5-(2-pyridyl)-3H-1,4-benzodiazepin-2-yl]hydrazone In the manner given in Example 1, 2-hydrazino-5-(2-pyridyl)-3H-1,4-benzodiazepine can be reacted with 1,1-dimethoxy-2-propanone in tetrahydrofuran to give 1,1-dimethoxy-2-propanone, 2-[7-chloro-5-(2-pyridyl)-3H-1,4-benzodiazepin-2-yl]hydrazone.

EXAMPLE 24

9-Chloro-1,5-dihydro-2-methyl-7-(2-pyridyl)-as-triazino[4,3-a][1,4]benzodiazepin-1-ol In the manner given in Example 2, 1,1-dimethoxy-2-propanone, 2-[7-chloro-5-(2-pyridyl)-3H-1,4-benzodiazepin-2-yl]hydrazone can be treated at 0° C. under nitrogen with concentrated sulfuric acid to give 9-chloro-1,5-dihydro-2-methyl-7-(2-pyridyl)-as-triazino[4,3-a][1,4]benzodiazepin-1-ol.

EXAMPLE 25

1,1-Diethoxy-2-propanone, 2-[9-trifluoromethyl-5-(2-pyridyl)-3H-1,4-benzodiazepin-2-yl]hydrazone In the manner given in Example 1, 9-trifluoromethyl-2-hydrazino-5-(2-pyridyl)-3H-1,4-benzodiazepine can be reacted with 1,1-diethoxy-2-propanone in tetrahydrofuran to give 1,1-diethoxy-2-propanone, 2-(9-trifluoromethyl-5-(2-pyridyl)-3H-1,4-benzodiazepin-2-yl)hydrazone.

EXAMPLE 26

11-Trifluoromethyl-1,5-dihydro-2-methyl-7-(2-pyridyl)-as-triazino[4,3-a][1,4]benzodiazepin-1-ol In the manner given in Example 2, 1,1-diethoxy-2-propanone, 2-[9-trifluoromethyl-5-(2-pyridyl)-3H-1,4-benzodiazepin-2-yl]hydrazone can be treated at 0° C. under nitrogen with concentrated sulfuric acid to give 11-trifluoromethyl-1,5-dihydro-2-methyl-7-(2-pyridyl)-as-triazino[4,3-a][1,4]benzodiazepin-1-ol.

In the manner given in Example 1, other 1,1-dialkoxy-2-alkanone, 2-(5-aryl-3H-1,4-benzodiazepin-2-yl)hydrazones of formula III can be synthesized by reacting a selected 2-hydrazino-5-aryl-3H-1,4-benzodiazepine (I) with a selected alkanone of formula III. Representative compounds, that can be thus produced, include: 1,1-dipropoxy-2-propanone, 2-[7-trifluoromethyl-(o-fluorophenyl)-3H-1,4-benzodiazepin-2-yl]hydrazone; 1,1-dimethoxy-2-propanone, 2-[8-trifluoromethyl-5-(o-fluorophenyl)-3H-1,4-benzodiazepin-2-yl]hydrazone; 1,1-diethoxy-2-butanone, 2-(9-bromo-5-phenyl-3H-1,4-benzodiazepin-2-yl)hydrazone; 1,1-diethoxy-2-pentanone, 2-[6-chloro-5-(o-chlorophenyl)-3H-1,4-benzodiazepin-2-yl]hydrazone; 1,1-diethoxy-2-butanone, 2-[7-nitro-5-(o-chlorophenyl)-3H-1,4-benzodiazepin-2-yl]hydrazone; 1,1-dimethoxy-2-pentanone, 2-(9-nitro-5-phenyl-3H-1,4-benzodiazepin-2-yl)hydrazone; 1,1-dipropoxy-2-butanone, 2-[8-bromo-5-(2,6-difluorophenyl)-3H-1,4-benzodiazepin-2-yl]hydrazone; 1,1-dimethoxy-2-butanone, 2-[6-chloro-5-(2,6-difluorophenyl)-3H-1,4-benzodiazepin-2-yl]hydrazone; 1,1-diethoxy-2-butanone, 2-[6-bromo-5-(2-pyridyl)-3H-1,4-benzodiazepin-2-yl]hydrazone; 1,1-dipropoxy-2-pentanone, 2-[8-bromo-5-(2-pyridyl)-3H-1,4-benzodiazepin-2-yl]hydrazone; 1,1-dimethoxy-2-butanone, 2-[6-trifluoromethyl-5-(2-pyridyl)-3H-1,4-benzodiazepin-2-yl]hydrazone; 1,1-diethoxy-2-butanone, 2-[6-chloro-5-(2-pyridyl)-3H-1,4-benzodiazepin-2-yl]hydrazone; 1,1-diethoxy-2-pentanone, 2-[6-nitro-5-(2-pyridyl)-3H-1,4-benzodiazepin-2-yl]hydrazone; 1,1-dipropoxy-2-butanone, 2-[8-nitro-5-(2-pyridyl)-3H-1,4-benzodiazepin-2-yl]hydrazone; and the like.

In the manner given in Example 2, other 1,5-dihydro-2-alkyl-7-phenyl-as-triazino[4,3-a][1,4]benzodiazepin-1-ols (IV) can be synthesized by reacting a selected 1,1-dialkoxy-2-alkanone, 2-(5-aryl-3H-1,4-benzodiazepin-1-yl)hydrazone (III) with concentrated sulfuric acid. Representative compounds, that can be thus obtained, include: 9-trifluoromethyl-1,5-dihydro-2-methyl-7-(o-fluorophenyl)-as-triazino[4,3-a][1,4]benzodiazepin-1-ol; 10-trifluoromethyl-1,5-dihydro-2-methyl-7-(o-fluorophenyl)-as-triazino[4,3-a][1,4]benzodiazepin-1-ol; 11-bromo-1,5-dihydro-2-ethyl-7-phenyl-as-triazino[4,3-a][1,4]benzodiazepin-1-ol; 8-chloro-1,5-dihydro-2-propyl-7-(o-chlorophenyl)-as-triazino[4,3-a][1,4]benzodiazepin-1-ol; 9-nitro-1,5-dihydro-2-ethyl-7-(o-chlorophenyl)-as-triazino[4,3-a][1,4]benzodiazepin-1-ol; 11-nitro-1,5-dihydro-2-propyl-7-phenyl-as-triazino[4,3-a][1,4]benzodiazepin-1-ol; 10-bromo-1,5-dihydro-2-ethyl-7-(2,6-difluorophenyl)-as-triazino[4,3-a][1,4]benzodiazepin-1-ol; 8-chloro-1,5-dihydro-2-ethyl-7-(2,6-difluorophenyl)-as-triazino[4,3-a][1,4]benzodiazepin-1-ol; 8-bromo-1,5-dihydro-2-ethyl-7-(2-pyridyl)-as-triazino[4,3-a][1,4]benzodiazepin-1-ol; 10-bromo-1,5-dihydro-2-propyl-7-(2-pyridyl)-as-triazino[4,3-a][1,4]benzodiazepin-1-ol; 8-trifluoromethyl-1,5-dihydro-2-ethyl-7-(2-pyridyl)-as-triazino[4,3-a][1,4]benzodiazepin-1-ol; 8-chloro-1,5-dihydro-2-ethyl-7-(2-pyridyl)-as-triazino[4,3-a][1,4]benzodiazepin-1-ol; 11-nitro-1,5-dihydro-2-propyl-7-(2-pyridyl)-as-triazino[4,3-a][1,4]benzodiazepin-1-ol; 10-nitro-1,5-dihydro-2-ethyl-7-(2-pyridyl)-as-triazino[4,3-a][1,4]benzodiazepin-1-ol; and the like.

Treating the compounds of formula IV with pharmacologically acceptable acids such as hydrochloric, hydrobomic, phosphoric, sulfuric, acetic, propionic, toluenesulfonic, methanesulfonic, tartaric, citric, lactic, malic, maleic, and cyclohexanesulfamic acids produces the pharmacologically acceptable salts of these compounds of formula IV which can be used like the free base compounds of formula IV. Salt formation is achieved in conventional manner by reacting the compounds of formula IV with excess of a selected acid in a suitable medium, e.g., water, a lower alkanol, ether, or acetone and recovering the salt by evaporating the solvent, preferably in vacuo.

I claim:

1. A compound of the formula IV:

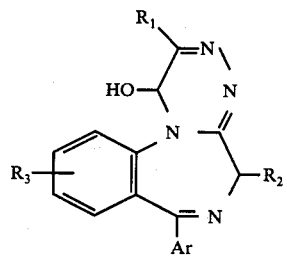

wherein $R_1$ is alkyl of 1 to 3 carbon atoms, inclusive; wherein $R_2$ is hydrogen, methyl or ethyl; wherein $R_3$ is hydrogen, fluoro, chloro, bromo, nitro or -$CF_3$; and wherein Ar is phenyl, o-chlorophenyl, o-fluorophenyl, 2,6-difluorophenyl, or 2-pyridyl, or the pharmacologically acceptable acid addition salts thereof.

2. A compound according to claim 1 wherein $R_1$ is methyl, $R_2$ is hydrogen, Ar is 2-pyridyl, $R_3$ is 9-bromo and the compound is therefore 9-bromo-1,5-dihydro-2-methyl-7-(2-pyridyl)-as-triazino[4,3-a][1,4]benzodiazepin-1-ol.

3. A compound according to claim 1 of formula IVa:

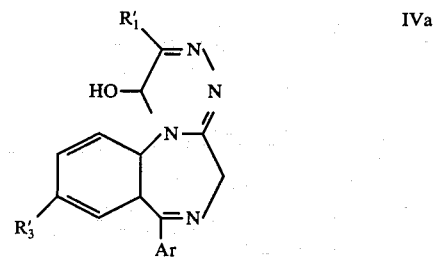

wherein $R_1'$ is methyl or ethyl; wherein $R_3'$ is fluoro, chloro, bromo, or trifluoromethyl; and wherein Ar is phenyl, o-chlorophenyl, o-fluorophenyl, 2,6-difluorophenyl or 2-pyridyl, or the pharmacologically acceptable acid addition salts thereof.

4. A compound according to claim 1 of formula IVb:

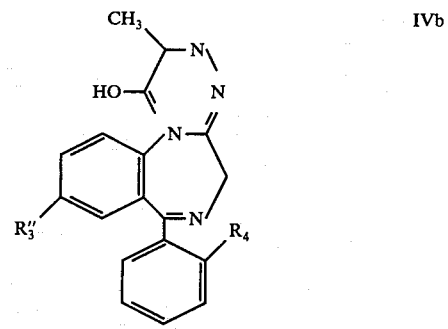

wherein $R_3''$ is fluoro, chloro or trifluoromethyl, and wherein $R_4$ is hydrogen, chloro or fluoro, or the pharmacologically acceptable acid addition salts thereof.

5. A compound according to claim 4 wherein $R_3''$ is chloro, $R_4$ is hydrogen, and the compound is therefore 9-chloro-1,5-dihydro-2-methyl-7-phenyl-as-triazino[4,3-a][1,4]benzodiazepin-1-ol.

6. A compound according to claim 4 wherein $R_3''$ and $R_4$ are chloro, and the compound is therefor 9-chloro-7-(o-chlorophenyl)-2,5-dihydro-2-methyl-as-triazino[4,3-a][1,4]benzodiazepin-1-ol.

7. A compound according to claim 4 wherein $R_3''$ is hydrogen, $R_4$ is chloro and the compound is therefore 7-(o-chlorophenyl)-1,5-dihydro-2-methyl-as-triazino-[4,3-a][1,4]benzodiazepin-1-ol.

8. A compound according to claim 4 wherein $R_3''$ is fluoro, $R_4$ is chloro and the compound is therefore 9-fluoro-7-(o-chlorophenyl)-1,5-dihydro-2-ethyl-as-triazino[4,3-a][1,4]benzodiazepine.

9. A process for the production of a compound of formula IV:

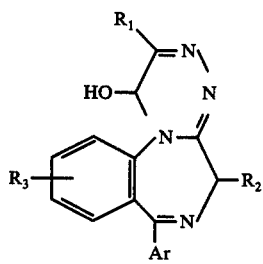

wherein $R_1$ is alkyl of 1 to 3 carbon atoms, inclusive; wherein $R_2$ is hydrogen, methyl or ethyl; wherein $R_3$ is hydrogen, fluoro, chloro, bromo, nitro or —$CF_3$; and wherein Ar is phenyl, o-chlorophenyl, o-fluorophenyl, 2,6-difluorophenyl, or 2-pyridyl, which comprises: treating a hydrazino compound of the formula

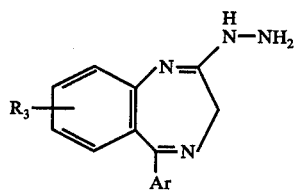

with a carbonyl compound II:

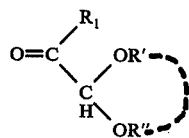

wherein $R_1$ is defined as above, and R′, R″ are alkyl of 1 to 3 carbon atoms, inclusive, or the group

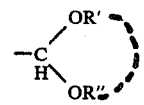

is a cyclic acetal, of the formula:

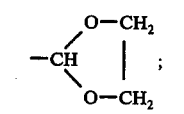

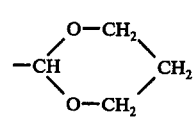

or

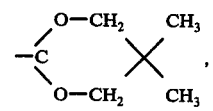

to give a compound of formula III:

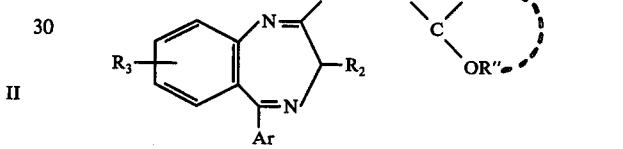

wherein $R_1$, $R_2$, $R_3$, R′, R″ and Ar are defined as above and cyclizing III to give the compound IV above.

10. The process of claim 9, wherein the cyclization reagent is concentrated sulfuric acid.

* * * * *

UNITED STATES PATENT OFFICE
CERTIFICATE OF CORRECTION

Patent No. 4,086,230      Dated 25 April 1978

Inventor(s) Gerald M. Evenson

It is certified that error appears in the above-identified patent and that said Letters Patent are hereby corrected as shown below:

Column 12, line 65, "1,5-dihydro-2-ethyl-" should read -- 1,5-dihydro-2-methyl- --.

*Signed and Sealed this*

*Eleventh* Day of *December 1979*

[SEAL]

*Attest:*

*Attesting Officer*

SIDNEY A. DIAMOND

*Commissioner of Patents and Trademarks*